United States Patent [19]

Fischer et al.

[11] 4,347,113
[45] Aug. 31, 1982

[54] OXYGEN CONTENT EXHAUST GAS SENSOR, AND METHOD OF ITS MANUFACTURE

[75] Inventors: Hermann Fischer, Stuttgart; Karl-Hermann Friese, Leonberg; Hans-Ulrich Gruber, Gerlingen; Wolfgang Heinemann, Weissach; Günter Knoll, Stuttgart; Ernst Linder, Mühlacker; Helmut Maurer, Schwieberdingen; Rainer Noack, Markgröningen; Leo Steinke, Waiblingen-Hegnach; Lothar Weber, Stuttgart; Helmut Weyl, Schwieberdingen, all of Fed. Rep. of Germany

[73] Assignee: Robert Bosch GmbH, Stuttgart, Fed. Rep. of Germany

[21] Appl. No.: 133,811

[22] Filed: Mar. 25, 1980

[30] Foreign Application Priority Data

Apr. 5, 1979 [DE] Fed. Rep. of Germany ....... 2913633

[51] Int. Cl.³ .............................................. G01N 27/58
[52] U.S. Cl. .............................. 204/195 S; 427/126.2
[58] Field of Search ......................... 204/195 S, 1 S; 427/126.2

[56] References Cited

U.S. PATENT DOCUMENTS 3,843,400 10/1974 Radford et al. ............. 204/195 S X
3,978,006 8/1976 Topp et al. .................... 252/477 R
4,199,425 4/1980 Sinkevitch .................... 204/195 S

FOREIGN PATENT DOCUMENTS 2206216 12/1978 Fed. Rep. of Germany .

Primary Examiner—G. L. Kaplan
Attorney, Agent, or Firm—Frishauf, Holtz, Goodman & Woodward

[57] ABSTRACT

To improve operation and output voltage, particularly at 400° C. and less, an oxygen sensor, especially adapted to determine oxygen content of automotive exhaust gases, is constructed by utilizing two electrodes applied on a body of stabilized zirconium dioxide, for example a closed tube, by making an electrode exposed to the exhaust gases in form of a mixture of finely dispersed ceramic material and a platinum-rhodium alloy, the ceramic material being present at about 40% (by volume) and 60% (by volume) platinum-rhodium alloy of 50-94% platinum and 50-6% rhodium (by weight). The second electrode, exposed to a reference gas comprises an alloy of palladium and another noble metal in a ratio of about 19-90% (by weight) Pd and 81-10% (by weight) noble metal. This electrode may also contain up to 40% (by volume) finely dispersed ceramic material. The electrode exposed to the exhaust gases is covered with a porous coating. The electrodes can be applied as aqueous or organic solutions of soluble noble metal compounds or suspensions, colloidal suspensions, with organic solvents, and the like, and subsequent sintering.

18 Claims, 1 Drawing Figure

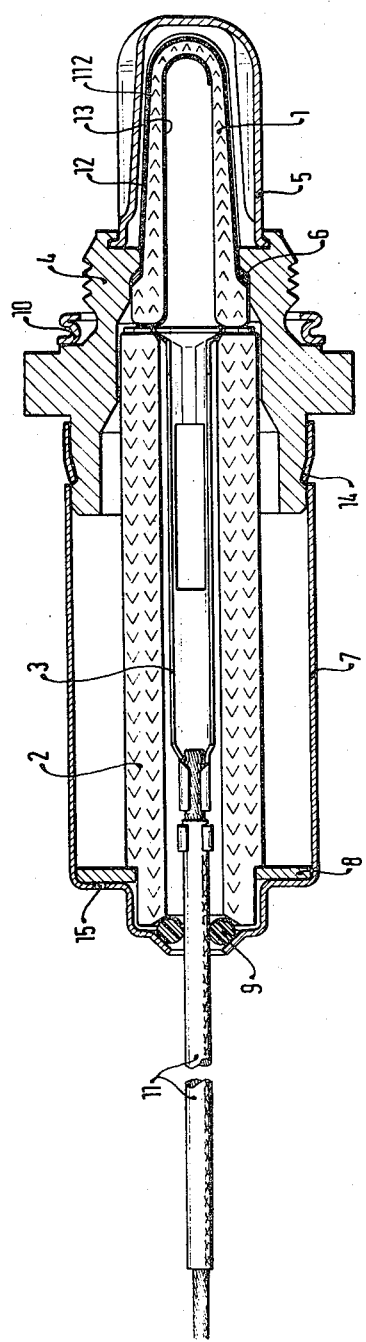

OXYGEN CONTENT EXHAUST GAS SENSOR, AND METHOD OF ITS MANUFACTURE

Reference to related application and patent: U.S. Ser. No. 098,708, filed Nov. 29, 1979, now U.S. Pat. No. 4,283,441, HAECKER et al; U.S. Pat. No. 4,021,326, POLLNER et al, both assigned to the assignee of the present application.

The present invention relates to an electrochemical sensor, and more particularly to a sensor to determine the oxygen content in the gases resulting from combustion processes, particularly exhaust gases from an internal combustion engine, and especially of the automotive type.

BACKGROUND AND PRIOR ART

Oxygen sensors customarily include electrodes applied to the solid electrolyte body, for example made of stabilized zirconium dioxide, to which electrodes are applied. In one form, one electrode is exposed to the gas to be measured, whereas the second electrode is applied to a surface of the solid electrolyte body which is exposed to a substance providing a reference oxygen concentration, for example to ambient air. To protect the solid electrolyte body, and the electrode exposed to the combustion gases, it has been proposed to apply a porous ceramic layer over the electrode and over the ceramic body at the side or surface exposed to the exhaust gases. In one form, the body is a closed tube. Reference is made to U.S. Pat. No. 4,021,326, Pollner et al, assigned to the assignee of the present application, describing such a sensor.

The electrodes of sensors of this type usually are made of platinum. It has also been proposed to make that electrode which is exposed to the gas to be measured, typically the exhaust gas from an internal combustion engine, of a platinum-rhodium alloy. Little attention has been given to the electrode which is exposed to the reference substance, typically ambient air, since that particular electrode is not of substantial importance for the operation or function of the sensor. It has been noted that the output from the sensors could still be improved, that is, that the conversion of the oxygen in the gas to be measured to an electrical signal could be better. This means that formation of the thermodynamic equilibrium of the gas at the electrode exposed to the gas to be measured is not achieved as well as would be desired. Consequently, the voltage difference which is being measured does not approach the value which is to be theoretically expected if the oxygen content of the gas to be sensed is low.

THE INVENTION

It is an object to so construct the sensor, and particularly to so construct the electrodes of a sensor that the conversion effectiveness at the electrode exposed to the gas to be measured, and consequently the voltage difference, is improved.

Briefly, the electrode exposed to the gas to be measured is made of a mixture of a platinum-rhodium alloy with a powdery or finely dispersed ceramic material forming a support structure or a support lattice therefor; the second electrode, exposed to a reference substance, typically ambient air or, rather, the oxygen therein, is made of a palladium—noble metal alloy.

In a preferred form, both electrodes have a support structure and the second, usually inner electrode on a tubular solid electrolyte body, exposed to the reference substance, is formed with a roughened or coarse-textured surface. A typical electrode to be exposed to the exhaust gases has, for example, 50 to 94% Pt and 50 to 6% rhodium (by weight), preferably about 88% platinum and 12% rhodium in alloyed form or as heterogeneous mixtures; this alloy or mixture is mixed with a support structure or support lattice material of stabilized zirconium dioxide or aluminum oxide in a ratio of, for example, about 60% (by volume) of the Pt-Rh alloy and 40% of ceramic. The second, usually inner, electrode within a closed tubular body for example is a palladium-platinum alloy of from 19% to 90% palladium and 81% to 10% platinum (by weight), preferably about 69% palladium and 31% platinum, mixed in about the same proportion with aluminum oxide or, preferably zirconium dioxide powder, so that the second electrode will have about 60% palladium-platinum alloy and 40% stabilized zirconium dioxide powder (by volume). The second electrode may also consist of a palladium-silver alloy containing about 9 to 70% (by weight) silver. The electrodes may have the form of a conductive track; and the solid electrolyte may be coated at least in part by a layer of a noble metal or by a mixture of several noble metals, covering the conductive track.

In accordance with a feature of the invention, the sensor can be made by applying the respective electrodes to the solid electrolyte body, then sintering the body and then applying a cover coating of a noble metal, or a mixture of several noble metals, using noble metal compounds dissolved in water or organic solvents, or colloidal suspensions of noble metals, or suspensions of noble metal powders, which are applied and sintered at a lower temperature over the previously sintered tubular body. A ceramic cover coating is applied over the outside of the tubular body.

In accordance with another feature of the invention, the electrodes as aforesaid are applied, and the outer or first electrode is covered with a powdered ceramic material such as magnesium spinel, or aluminum oxide, possibly with the additive of a pore-forming substance which, upon heating, will evolve and leave the material in porous form.

The operating response of the sensor, particularly at lower temperatures, that is, below about 400° C., can be improved by forming the electrodes, and particularly the electrode exposed to the reference gas in the form of a conductive track. If the solid electrolyte body is a closed tube, this would, normally, be the inner electrode, exposed to ambient air. The solid electrolyte then has a layer of a noble metal applied thereto which determines the thermodynamic gas equilibrium. Rather than using a noble metal, a mixture of various noble metals may be used, all covering the conductive track. The conductive tracks, then, act not only as electrical connection leads but, additionally, as electrodes, at which electrochemical reaction will occur. The electrochemical reaction is improved by applying the additional layer or coating of noble metal, or a mixture thereof.

High catalytic activity of additional noble metal electrode layers is obtained by sintering them at temperatures which are preferably not much above the maximum operating temperatures to which the sensor will be exposed when in use but, in any event, which are below the sinter temperature of a solid electrolyte body. Suitable elements to form pores are carbon black, $(NH_4)_2CO_3$, or other substances which can burn out, evaporate, or evolve, and generate a porous structure so that the pore structure of the additional electrode layer is desirably affected. Such a hybrid electrode combines the advantages of an excellently adhering electrode arrangement in form of a conductive track with a catalytically highly active electrode layer.

The sensor has the advantage that it is capable of higher conversion that is, enhanced electrochemical action, of the gas to be measured at the electrode exposed to this gas, thus increasing the voltage difference of the output. It has been found that the level of voltage, that is, the voltage if the gases are reducing, depends to a great extent on the formation of the electrode exposed to the reference substance, typically the reference gas, that is, ambient air or, rather, the oxygen therein.

DRAWINGS

Wherein the single FIGURE is a highly schematic longitudinal sectional view through a sensor embodying the invention, in which the sensing element is in the shape of a tube closed at one end, the outer surface of which is exposed to the gas to be measured and the inner surface is exposed to a reference gas. The sensor illustrated in the drawing is particularly adapted for assembly in the exhaust gas system of an automotive-type internal combustion engine and to determine the λ-value, that is, the oxygen content in the exhuast gases to sense if the gases are reducing or oxidizing. The construction is so arranged that it can be directly screwed into a suitably tapped opening in the exhaust manifold or elsewhere in the exhaust gas system and can be connected by a connection cable to an electronic evaluation circuit and, if desired, further to control systems which regulate the fuel-air mixture to the engine so that it will operate with a fuel-air relationship close to a predetermined ratio.

DETAILED DESCRIPTION OF AN EXAMPLE

The sensor element itself is a tube 1 of stabilized zirconium dioxide, closed at one end. The tube 1, at its outer surface, has a layer system which includes an electrode 12 directly applied to the solid electrolyte body 1. The electrode 12 consists of a platinum-rhodium alloy having 12% rhodium and 88% platinum (by weight); it is mixed with stabilized zirconium dioxide powder to form a mixture containing 40% (by volume) stabilized zirconium dioxide powder (see German Pat. No. 22 06 216 to which U.S. Pat. No. 3,978,006, Topp et al., corresponds) and 60% (by volume) of the Pt-Rh alloy powder. A porous ceramic protective coating 112 is applied over the electrode. The ceramic coating 112, for example, consists of magnesium spinel—see the referenced U.S. Pat. No. 4,021,326, Pollner et al. The upper end of tube 1 carries a flange which is engaged by a sealing ring 6 to form a seat in housing 4.

The inner, or second, electrode 13 is exposed to a reference gas, in the embodiment to ambient air. It consists of a palladium-platinum alloy containing 31% platinum (by weight); the alloy itself is mixed with a ratio of 60% with 40% stabilized zirconium dioxide powder (by volume). It is carried around the rounded edge at the open end of the body and, after application, has its surface roughened. The inner electrode 13 is electrically connected by a connecting element 3 made of high temperature-resistant, e.g. refractory metallic material. The connecting element 3 is pressed with its lower end, shaped in form of a plate or connected to a contact plate, against the portion of the inner electrode 13 which is carried around the edge of the tube 1. The contact plate is formed with slits in order to permit ingress of ambient air as a reference gas to the interior of the tube 1. The upper portion of the connecting element 3 is shaped to receive a connection cable 11. A ceramic tube 2, made of aluminum oxide ceramic material, is located around the cable and the connecting element 3, pressed against the contact dish or disk of the contact terminal 3. The pressure on the ceramic tube 2 is effected by a protective sleeve 7 which is connected to the housing 4 by inwardly punched tabs 14. A disk or dish spring 8 is located between the ceramic tube 2 and an in-turned ridge of the sleeve 7 to ensure good contact pressure, and engagement of the contact disk of the contact element 3 with the inner electrode 13. The sleeve 7, forming part of the housing, is formed with a bore 15 in the region of the spring 8 which permits ventilation of the space within the tube 1. A sealing ring 9 positioned around the cable prevents penetration of dirt or dampness or moisture into the interior of the sensor and additionally protects the connecting cable 11 against kinks and sharp bends. The outer surface of the closed tube 1 is protected by a slotted protective sleeve 5, made of heat-resistant steel, which is set into the housing 4 by a flange connection. The housing 4 additionally includes a sealing ring 10, just above the threaded portion, to permit screwing the sensor into a suitably tapped opening, and insuring a tight, sealed connection between the housing 4 and the relevant part of the exhaust system of the engine with which the sensor is to be used.

The operation of the electrodes, particularly of the inner electrode 13 exposed to the reference gas can be improved by forming the electrode in the shape of a conductive track over which a layer of a noble metal or a mixture of various noble metals is applied on the solid electrolyte tube 1. The area of the layer is larger than the area of the conductive track. This particularly improves the operation of the sensor at low temperatures, i.e. below 400° C., and especially at start-up conditions. The conductive track will act as a conductor as well as an electrode. It has excellent adhesion on the solid electrolyte body. The additional coating or layer of noble metal ensures rapid and effective conversion at the three-phase boundary and results in quick setting of thermodynamic equilibrium. The excellent adhesion of the conductive track on the solid electrolyte body 1 is one of the big advantages of this structure.

Catalytically active electrode layers in the active region of the sensor can be constructed this way:

Noble metals, suspended in water, or noble metal compounds dissolved in water or in organic solvents, colloidal suspensions of noble metals, powdered noble metals in suspensions, for example with adhesion-promoting substances, or combinations of such suspensions and solutions, are applied to the respective zones or regions of the solid electrolyte body. They are sintered at temperatures which, preferably, are not or only slightly over the later maximum operating temperatures of the sensor. The solutions and suspensions can be dried or blown, after application, with a stream of air in order to obtain a fine distribution. Additives which form pores, such as carbon black, (NH4)2CO3, and the like, can be mixed therewith. Examples ae shown in the subsequent tables.

As a typical example:
a 15% rhodium resinate solution and 70% platinum suspension are mixed in such a manner that a relationship of Pt to Rh of 90:10 (by weight) is obtained. Other mixtures can be used, for example 50 parts platinum and 50 parts palladium (by weight).

Electrode layers for anodic oxidation of oxygen on a reference electrode which are particularly advantages are porous layers which contain the noble metal of silver. Examples for electrodes which are particularly well adherent and excellently suitable for construction in conductive track form are shown in Table 1; examples for catalytically highly active electrode layers are shown in Table 2.

The electrochemically effective portion of the sensor can be made in various ways. In accordance with a feature of the invention, the electrochemically active portion of a sensor in which both electrodes 12 and 13 are made as described, can be made by sequential steps as follows:

1. A presintered solid electrolyte body, in tubular form, closed at one end, and made of stabilized zirconium dioxide, is provided.

1.1 A first electrode in form of a conductive track (see Table 1) is applied to the outside; this electrode is a platinum-rhodium alloy, e.g. 88% platinum and 13% rhodium (by weight) mixed with finely divided zirconium dioxide, forming the ceramic component, in a ratio of about 60% platinum-rhodium alloy and 40% stabilized zirconium dioxide powder (by volume).

1.2 A second electrode is applied in form of a conductive strip at the inside surface, comprising a palladium-platinum alloy, for example about 69% palladium and 31% platinum (by weight) which, preferably, is also mixed with stabilized zirconium dioxide powder in a ratio of 60% palladium-platinum alloy and 40% zirconium dioxide (by volume).

2. The solid electrolyte body with the outer electrode strip or track and the second or inner electrode strip or track thereon is sintered at between about 1400° to 1700° C., preferably closer to the lower temperature, for example at about 1500° C.

3. A layer of a noble metal (see Table 2), or a mixture of various noble metals, is applied over each one of the conductive tracks at least at the end portion of the sensor, that is, in the sensor region by the following procedures:

3.1 Noble metal compounds suspended or dissolved in water or organic solvents may be applied; or 3.2 noble metals in colloidal suspension form can be applied; or 3.3 suspensions of noble metal powders can be applied.

4. The noble metal or noble metal compound is dispersed by a stream of air or an air blast. This step is not strictly necessary if the layer being applied is sufficiently dispersed and thin enough upon application.

5. The applied layer is sintered at between 800° to 1300° C.

6. The outer surface on which the electrode is applied has a porous ceramic protective layer applied thereover. This layer may, for example, be magnesium spinel or aluminum oxide, if needed combined with a foaming or pore-forming substance.

The noble metal or mixed noble metal layer—step 3 in the foregoing example—may be in form of a noble metal resinate a noble metal acetylacetonate e.g. a noble metal complex salt of acetylacetone in organic solvents and/or a noble metal suspension.

The sensors can also be made by constructing the outer electrode 12 as well known, and for example as described in the referenced U.S. patent, and only constructing the inner electrode 13 in different form. If this type of sensor is desired, the following method steps are suitable:

1. A presintered solid electrolyte body of stabilized zirconium dioxide in form of a closed tube is provided.

1.1 The first, outer, electrode 12 is applied, consisting of a platinum-rhodium alloy with a finely dispersed ceramic material, as in the above example.

1.2 A second electrode in form of a conductive track of a palladium alloy is applied preferably, but not necessarily, with the addition of finely dispersed ceramic material, as in the above example.

2. To provide a porous ceramic cover layer over the first electrode, a powdered ceramic material such as magnesium spinel, or aluminum oxide, if necessary with the addition of a foaming or pore-forming substance is applied over the first, or outer, electrode 12.

3. The solid electrolyte body with the electrode layers applied is sintered at a temperature of between 1400° to 1700° C., for example at about 1500° C.

4. A layer comprising a noble metal or a mixture of various noble metals is applied to the inside of the tube covering the conductive track of the inner electrode 13, 4.1 the inner layer being made of a noble metal compound, dissolved in water or an organic solvent;

4.2 the inner layer being made of a colloidal dissolved noble metal; or 4.3 of a noble metal powder suspension.

5. The material forming
the inner layer is dispersed by an air blast or air stream—if needed; this is not a necessary step, but desirable to provide for uniform coating.

6. The layer is sintered at a temperature of between 800° to 1300° C.

The noble metal or mixed noble metal layer—step 4 in the foregoing example—may be in form of a noble metal resinate a noble metal acetylacetonate in organic solvents and/or a noble metal suspension.

Example in tabular form:

TABLE 1

| | | Conductive Tracks | | | | | |
| | | | Application on sensor body | | Sintering conditions equal or similar | | |
| Electron conductive components | Adhesion promoting substance | Ratio of Additives Vol. % | preheated to incandescence | sintered | electrode | glaze | ceramic |
| --- | --- | --- | --- | --- | --- | --- | --- |
| Pt-Suspension | CSZ* or VSZ-# powder | 60 Pt/40 CSZ or YSZ | x | | | | x |
| Pd-Suspension | CSZ or YSZ- powder | 60 Pd/40 CSZ or YSZ | x | (x) | | (x) | x |
| Pd-Suspension | Ba—Al—Silicate-glass | 75 Pd/25 Glass | | x | | x | |
| 60 Ag/40 Pd-Suspension (by | Ba—Al—Silicate-glass | 75 Ag-Pd/25 Glass | | x | | x | |

TABLE 1-continued

| Conductive Tracks | | | | | | | |
|---|---|---|---|---|---|---|---|
| | | | Application on sensor body | | Sintering conditions equal or similar | | |
| Electron conductive components | Adhesion promoting substance | Ratio of Additives Vol. % | preheated to incandescence | sintered | electrode | glaze | ceramic |
| weight) | | | | | | | |
| 60 Ag/40 Pd-Suspension (by weight) | — | — | | x | x | (x) | |
| 80 Pt/20 Rh-Suspension (by weight) | CSZ- or YSZ- powder | 60 Pt—Rh/40 CSZ or YSZ | x | | | | x |
| Perowskite-powder-Suspension | — | — | | x | | x | (x) |
| Pd-Suspension | Bi-Oxide(+Glass) | 90 Pd/10 Bi-Oxide | | x | (x) | x | |
| Pd/Pt-Suspension | CSZ- or YSZ- powder | 90 Pd—Pt/40 CSZ or YSZ | x | | | | x |
| Pt-Suspension | Glass | — | | x | | | |

*CaO Stabilized Zirconium Dioxide
Yttrium Stabilized Zirconiumdioxide
x = yes
(x) = possible

TABLE 2

| Electrode Layers - Application on sintered electrode body | | | |
|---|---|---|---|
| (a) Solution with catalyst (by weight) | (b) Suspension with catalyst (by weight) | Mixtures of (a) and (b) (by weight) | Sinter conditions |
| Rh-resinate (15% or 5%) | — | — | 800–1200° C. |
| Pt-resinate (8%) | — | — | 800–1000° C. |
| Pt 90-Rh 10-resinate | — | — | 800–1000° C. |
| Rh-resinate (15%) | Pt-Suspension (70%) | e.g. 90-Pt/10-Rh | 800–1200° C. |
| Pt-resinate (8%) | Ag-Suspension (50%) | e.g. 70 Ag/30 Pt | 800–1000° C. |
| Pt-resinate (8%) | Pt-Suspension (70%) | e.g. Pt 20 resinate/80 Susp. | 800–1000° C. |
| — | 70 Ag/30 Pt-Suspension | — | 800–1000° C. |
| — | 30 Ag/70 Pt-Suspension | — | 900–1100° C. |
| —. | 10 Ag/90 Pt-Suspension | — | 900–1300° C. |
| — | 50 Pd/50 Pt-Suspension | — | 1100–1300° C. |
| — | 50 Ag/50 Pd-Suspension | — | 800–1200° C. |
| Solution of noble metal compounds (Pt group, silver) in organic phase (e.g. Pt-acetylacetonate) | — | — | 800–1000° C. |

A suitable suspension media for the platinum and palladium suspensions is terpineol.

The concentration of a suitable suspension, that is, the mixture of suspension medium to the respective metal composition, is in the range of 2–30% by volume, with a preferred range of 5–15% by volume of the metal.

Suitable noble metal compounds are the chlorides and bromides of the noble metals, the complex aminohalides of the general formula [M(NR$_3$)$_4$]X$_2$ with M=Pt, Pd, Rh; R=H, alkyl and X=Cl, Br and compounds of the noble metals with diketones which can be transformed to the enol-form, especially with 1,3-diketones, the most suitable of this group being the noble metal salts of the acetylacetone.

Suitable solvents for the noble metal compounds are water or dimethyl-formamide (DMF) and other solvents of high polarity. (high dielectric constant).

The noble metals, when in powder form, are preferably ground to a particle size in the range of 0.1 to 15 μm, measured by sedimentation analysis.

We claim:

1. Electrochemical sensor to determine the oxygen content in gases resulting from a combustion process, particularly exhaust gases from an internal combustion engine having a solid electrolyte body (1) comprising stabilized zirconium dioxide, having a first surface portion exposed to the combustion gases, and a second surface portion exposed to a reference substance of known oxygen concentration;

a first electrode (12) applied to said first surface portion;

a second electrode (13) applied to said second surface portion;

and a porous ceramic protective cover layer (112) covering the first electrode, and wherein, in accordance with the invention, the electrodes are characterized in that the first electrode comprises a mixture of powdery ceramic material, forming a support structure or support lattice, and a platinum-rhodium alloy;

and the second electrode comprises an alloy of palladium and another noble metal.

2. Sensor according to claim 1, wherein the platinum-rhodium alloy of the first electrode comprises an alloy of between 50 to 94% platinum and 50 to 6% rhodium, both by weight;

and wherein the second electrode comprises 19 to 90% palladium and 81 to 10% platinum, both by weight.

3. Sensor according to claim 2, wherein the alloy of the first electrode comprises about 88% platinum and 12% rhodium, both by weight;

and wherein the alloy of the second electrode comprises about 69% palladium and 31% platinum, both by weight.

4. Sensor according to claim 1, wherein the second electrode additionally include powdery ceramic material.

5. Sensor according to claim 4, wherein the ceramic material comprises at least one of the materials of the group consisting of: stabilized zirconium dioxide and aluminum oxide.

6. Sensor according to claim 5, wherein the first electrode has about 60% platinum-rhodium alloy and 40% stabilized zirconium dioxide powder;

and the second electrode has about 60% palladium-platinum alloy and 40% stabilized zirconium dioxide powder;

all proportions by volume.

7. Sensor according to claim 1, wherein the ceramic material comprises at least one of the materials of the group consisting of: stabilized zirconium dioxide and aluminum oxide.

8. Sensor according to claim 1, wherein the second electrode comprises a palladium-silver alloy having about 9 to 70%—by weight-silver.

9. Sensor according to claim 8, wherein the second electrode comprises a mixture of zirconium dioxide powder forming a support structure or lattice;

and the ratio of alloy to zirconium dioxide is about 60 to 40% by volume.

10. Sensor according to claim 1, wherein at least one of the electrodes has the form of a conductive track or path;

and a layer of noble metal applied to the solid electrolyte body and over the at least one electrode comprising a noble metal or a mixture of noble metals capable of catalyzing the thermodynamic equilibrium of gases to which the electrode and said layer are exposed.

11. Method to make an electrochemical sensor to determine the oxygen content in gases resulting from a combustion process, particularly the exhaust gases from an internal combustion engine, having a solid electrolyte body (1) comprising stabilized zirconium dioxide and having a first surface portion exposed to the gases and a second surface portion exposed to a reference substance of known oxygen concentration;

a first electrode (12) applied to said first surface portion;

a second electrode (13) applied to the second surface portion;

and a porous ceramic protective cover layer (112) covering the first electrode, said method comprising the steps of 1. providing a presintered solid electrolyte body comprising stabilized zirconium dioxide;

1.1 applying a platinum-rhodium alloy and powdery ceramic material to said first surface to form the first electrode, shaped in form of a conductive track;

1.2 applying a palladium-platinum alloy on the second surface to form the second electrode, shaped in form of a conductive track;

2. sintering the solid electrolyte body with the electrode layers applied thereto at a temperature of between about 1400° to 1700° C.;

3. supplying a layer of a noble metal or a mixture of noble metals over at least said second electrode and covering the second electrode at least in part, said noble metal or mixture of noble metals comprising at least one of the materials of the group of consisting of 3.1 noble metal alloys dissolved in water or organic solvents;

3.2 colloidal noble metal suspension;

3.3 powdered noble metal suspension;

4. sintering the layer of step 3 at a temperature of between about 800° C. to 1300° C.; and 5. applying the porous ceramic protective covering layer (112).

12. Method according to claim 11, wherein the step 1.2 comprises applying a mixture of a powdery ceramic material together with the palladium-platinum alloy to form the second electrode.

13. Method according to claim 11, further including the step of dispersing the layer applied in step 3 on the respective surface of the solid electrolyte body with a stream or blast of air before the sintering step 4.

14. Method according to claim 11, wherein the noble metal or noble metal layer applied in step 3 is applied to both surface portions of the solid electrolyte body covering, at least in part, both of the electrodes;

and the step of applying the porous ceramic layer is carried out after step 4 by applying the material of said porous layer on the noble metal or noble metal mixture layer applied in step 3 and over the electrode at said first surface portion.

15. Method according to claim 11, wherein the step of applying the layer of noble metal or mixture of noble metals of step 3 comprises applying said layer only on the second surface portion of the solid electrolyte body and over the second electrode (13);

and the step of applying the porous ceramic protective cover layer (112) is carried out in advance of the sintering step, step 2, to sinter the porous ceramic layer and the electrode layer together.

16. Method according to claim 15, wherein the step of applying the porous ceramic protective cover layer comprises applying a layer of pulverized material comprising at least one of the materials of the group consisting of magnesium spinel and aluminum oxide.

17. Method according to claim 16, further including the step of adding a pore forming substance to said material forming the porous ceramic protective cover layer (112) prior to sintering thereof.

18. Method according to claim 11, wherein the step of applying the noble metal or mixture of noble metals of step 3 comprises applying to the respective surface portion of the solid electrolyte body at least one of the materials of the group consisting of: noble metal resin ester; noble metal acetylacetonate in an organic binder and a noble metal suspension.

* * * * *